(12) United States Patent
Wales et al.

(10) Patent No.: US 12,253,388 B2
(45) Date of Patent: Mar. 18, 2025

(54) ENDOSCOPIC POSITIONING ENCODER

(71) Applicant: Boston Scientific Scimed, Inc., Maple Grove, MN (US)

(72) Inventors: Ryan V. Wales, Northborough, MA (US); Morgan Zhu, Somerville, MA (US); Kurt Nicholas Robakiewicz, Upton, MA (US); Scott E. Brechbiel, Burlington, MA (US); Jeff Gray, Sudbury, MA (US)

(73) Assignee: Boston Scientific Scimed, Inc., Maple Grove, MN (US)

(\*) Notice: Subject to any disclaimer, the term of this patent is extended or adjusted under 35 U.S.C. 154(b) by 222 days.

(21) Appl. No.: 18/059,248

(22) Filed: Nov. 28, 2022

(65) Prior Publication Data
US 2023/0168109 A1    Jun. 1, 2023

Related U.S. Application Data

(60) Provisional application No. 63/284,287, filed on Nov. 30, 2021.

(51) Int. Cl.
| | | |
|---|---|---|
| *G01D 5/14* | (2006.01) | |
| *G01P 3/487* | (2006.01) | |
| *G06F 3/0362* | (2013.01) | |

(52) U.S. Cl.
CPC .............. *G01D 5/145* (2013.01); *G01P 3/487* (2013.01); *G06F 3/0362* (2013.01)

(58) Field of Classification Search
CPC ....... G01D 5/145; G01P 3/487; G06F 3/0362; A61B 34/30; A61B 90/16; A61B 2034/2051; A61B 2034/301; A61B 2090/062; A61B 2090/067; A61B 1/00147; A61B 34/20; G02B 23/2484
See application file for complete search history.

(56) References Cited

U.S. PATENT DOCUMENTS

| | | | |
|---|---|---|---|
| 8,932,063 B2 | 1/2015 | Taylor et al. | |
| 2007/0135803 A1 | 6/2007 | Belson | |
| 2011/0036356 A1* | 2/2011 | Arn | A61B 90/14 128/845 |
| 2013/0137963 A1* | 5/2013 | Olson | G16H 20/40 600/534 |

(Continued)

FOREIGN PATENT DOCUMENTS

| | | |
|---|---|---|
| WO | 2020040652 A1 | 2/2020 |
| WO | 2020257280 A1 | 12/2020 |

*Primary Examiner* — Christopher P Mcandrew
*Assistant Examiner* — Zannatul Ferdous
(74) *Attorney, Agent, or Firm* — Bookoff McAndrews, PLLC

(57) ABSTRACT

A system for tracking a medical device, the system comprising a support having a channel extending therethrough, the channel being defined circumferentially by a surface, at least one encoder configured to track movement of a medical device through the channel, and one or more processors configured to receive input from the at least one encoder, receive an instruction from a user to store a zero position of the medical device relative to the channel, determine relative movement of the medical device from the zero position, and communicate the relative movement of the medical device from the zero position.

17 Claims, 5 Drawing Sheets

(56) References Cited

U.S. PATENT DOCUMENTS

| | | | | |
|---|---|---|---|---|
| 2016/0038216 A1* | 2/2016 | Woo | ....................... | A61B 90/04 |
| | | | | 606/34 |
| 2017/0086927 A1 | 3/2017 | Auld et al. | | |
| 2017/0215762 A1* | 8/2017 | Burnside | .............. | A61B 5/6848 |
| 2021/0113275 A1 | 4/2021 | Coiseur | | |
| 2023/0355318 A1* | 11/2023 | Graveley | ............... | A61B 5/065 |

\* cited by examiner

ENDOSCOPIC POSITIONING ENCODER

CROSS-REFERENCE TO RELATED APPLICATIONS

This application claims the benefit of priority from U.S. Provisional Application No. 63/284,287, filed on Nov. 30, 2021, which is incorporated by reference herein in its entirety.

TECHNICAL FIELD

This disclosure relates generally to medical devices, systems, and methods for determining and/or maintaining a position of a medical device within a body. More particularly, embodiments of the present disclosure relate to the use of encoders for tracking positioning of an endoscope during endoscopic procedures.

BACKGROUND

Endoscope operators are performing more advanced procedures as their skill level increases and available technology advances. Endoscopic Retrograde Cholangiopancreatography (ERCP) is an advanced procedure that requires the physician to access the papilla. The papilla acts as the access point to the common bile duct. One challenge that physicians face is maintaining the position of an endoscope relative to the papilla. Physicians will get the endoscope into a desired position, but will lose said desired position by the time the wire or tome has been fed to the distal end of the endoscope. The inability to maintain or re-establish the desired position may account for about 50% of the time of the ERCP procedure and is often the most difficult aspect of the procedure. Failure to gain access to the papilla or repeated attempts to do so can result in enflaming the papilla, pancreatitis, or other adverse events.

SUMMARY OF THE DISCLOSURE

According to an example, a system for tracking a medical device may comprise a support having a channel extending therethrough, the channel being defined circumferentially by a surface, at least one encoder configured to track movement of a medical device through the channel, and one or more processors configured to receive input from the at least one encoder, receive an instruction from a user to store a zero position of the medical device relative to the channel, determine relative movement of the medical device from the zero position, and communicate the relative movement of the medical device from the zero position.

In another example, the at least one encoder may include a movable portion extending through or positioned at the surface defining the channel. Determining relative movement may include determining a proximal and/or a distal movement of the medical device relative to a proximal and/or distal position of the medical device at the zero position. Determining relative movement may include determining rotation of the medical device relative to a rotational orientation of the medical device at the zero position. The at least one encoder may include a first encoder wheel configured to measure proximal and/or distal movement, and a second encoder wheel configured to measure rotation of the medical device about a central longitudinal axis of the medical device. The at least one encoder may include a ball, and the at least one encoder is configured to measure proximal and/or distal movement and rotation of the medical device based on movement of the ball. The at least one encoder may include a magnet and Hall effect sensor configured to detect movement of the medical device. The support may be a bite block configured to be secured to the face and/or mouth of a patient. The system may further include a motor coupled to the one or more processors and to the medical device, wherein the one or more processors are further configured to move the medical device back to the zero position by activating the motor. Moving back to the zero position may include moving the medical device proximally and/or distally. Moving back to the zero position may include rotating the medical device. The motor may be configured to be coupled to the medical device via a wheel or ball. The wheel or ball may be separate from a wheel or ball that forms part of the encoder. The wheel or ball may be the same component as part of the encoder. Communicating the relative movement may include sending the relative proximal and/or distal displacement and sending the relative rotational displacement from the zero position to a display device.

According to an example, a system for tracking a medical device may comprise a support having a channel extending therethrough, the channel being defined circumferentially by a surface, at least one first wheel coupled to an encoder and configured to track movement of the medical device through the channel, at least one second wheel coupled to a motor and configured to drive the medical device through the channel, and one or more processors configured to receive input from the at least one encoder, receive an instruction from a user to store a zero position of the medical device relative to the channel, determine relative movement of the medical device from the zero position, and communicate the relative movement of the medical device from the zero position. A first wheel may drive the medical device to the zero position and a second wheel may track the displacement of the first wheel to ensure the medical device returns to the zero position in response to any deviation. The one or more processors may be configured to automatically move the medical device back to the zero position.

According to an example, a method for tracking a medical device may comprise receiving an instruction from a user to store a current, zero position of a medical device in the user, measuring movement of the medical device relative to the zero position, and moving the medical device back to the zero position. Measuring relative movement of the medical device relative to the zero position may include measuring the proximal and/or distal movement and rotation of the medical device relative to the zero position.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

The ability to maintain or re-establish a position relative to the papilla or to the space could reduce the time to conduct an ERCP procedure. At least some embodiments of the present disclosure relate to devices and methods for establishing a baseline position of an endoscope (e.g., a Zero Point position). Such devices and methods may help allow physicians to quickly and repeatedly re-gain positioning of a medical device such as an endoscope relative to any reference location within a patient's body, such as, e.g., the papilla during an ERCP procedure, track positioning within lung nodules in a bronchoscopic procedure, track positioning within a gastrointestinal tract of a patient during an endoscopic procedure, or the like.

Figure 1:
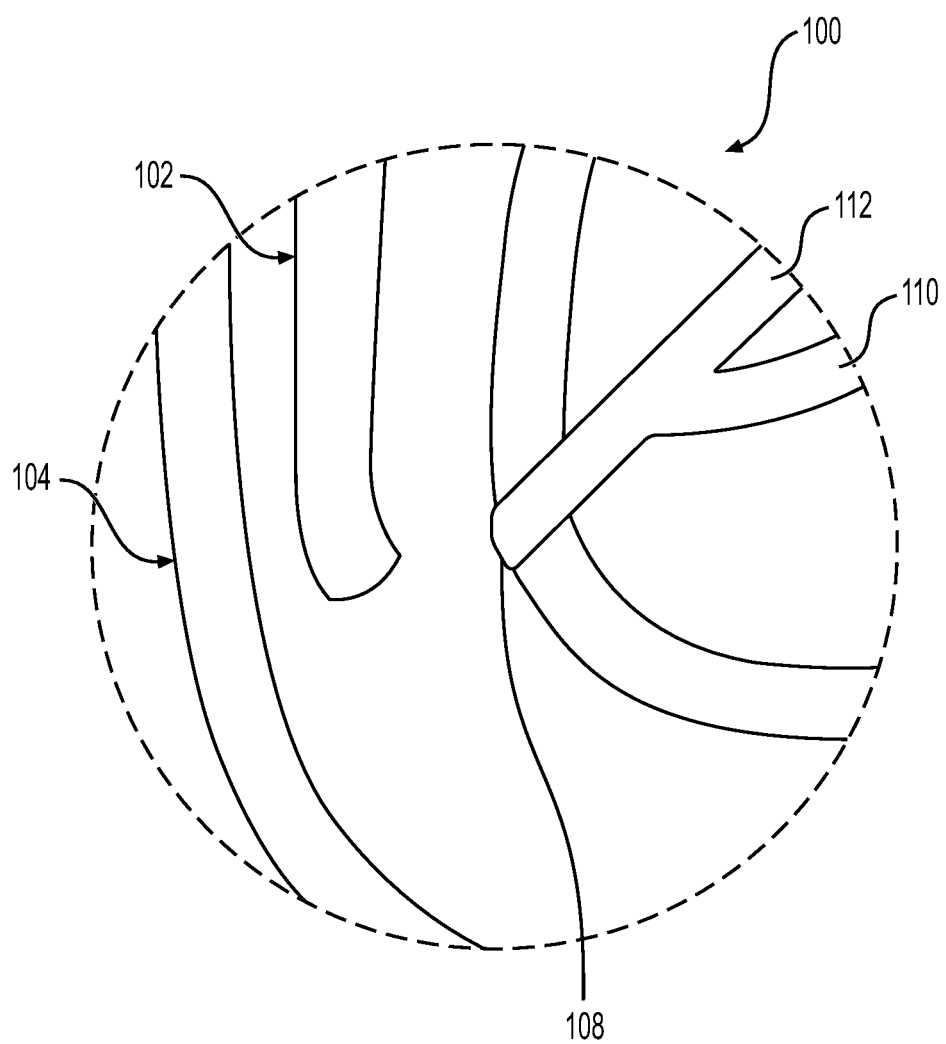
FIG. 1 illustrates the positioning of an endoscope relative to the papilla.

FIG. 1 illustrates a portion of a duodenum 104 where a papilla of Vater 108 is located in a system 100. The papilla of Vater 108 generally forms the opening where a pancreatic duct 110 and a bile duct 112 can empty into the duodenum 104. Endoscope 102 is shown advanced through the duodenum 104 and positioned next to the papilla of Vater 108.

Although the term endoscope may be used herein, it will be appreciated that other devices, including, but not limited to, duodenoscopes, colonoscopes, ureteroscopes, bronchoscopes, laparoscopes, sheaths, catheters, or any other suitable delivery device or medical device may be used in connection with the devices and methods of this disclosure.

Figure 2A:
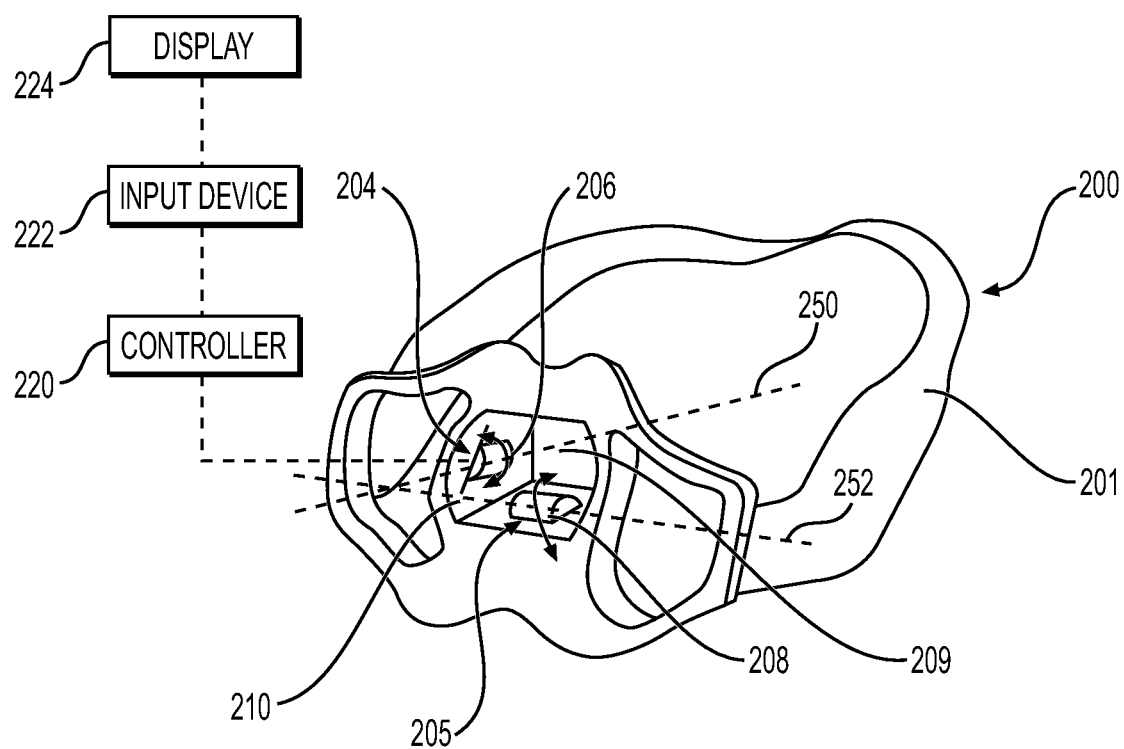
FIGS. 2A-2B illustrate an exemplary encoder system.

FIG. 2A depicts a bite block 200. Bite block 200 may be any suitable device used during a procedure to help ensure the patient's mouth remains open as well to protect an endoscope from damage. The bite block may be placed in the patient's mouth and also secured around the patient's head using a strap 201. Bite block 200 may include one or more encoders configured to determine and/or track the relative movement and/or position of an endoscope or other elongate medical device extending through a channel 209 of bite block 200. In the embodiment shown in FIGS. 2A-2B, bite block 200 includes an encoder 204 and an encoder 205. Channel 209 may be defined circumferentially by one or more surfaces. In one embodiment, channel 209 may have a generally circular cross-section, although other suitable cross-sections also are contemplated. Both encoder 204 and encoder 205 may extend through the surface 210 that defines channel 209. Encoder 204 may be configured to rotate about a first axis 250 and encoder 205 may be configured to rotate about a second axis 252 that is perpendicular to axis 250. First axis 250 may be substantially parallel with a central longitudinal axis of channel 209 that extends through channel 209 in the proximal-distal direction. Second axis 252 may extend laterally so that it extends substantially parallel to face of channel 209. Second axis 252 may be substantially perpendicular to first axis 250.

Endoscope 102 shown in FIG. 1, may be extended through channel 209 in the proximal-distal direction and also rotated within channel 209.

Encoder 204 and encoder 205 may be incremental or absolute encoders. Encoder 204 may be located on the left-side or right-side of channel 209 (e.g., a first circumferential position). Encoder 205 may be located on the top or bottom of channel 209 (e.g. a second circumferential position that is circumferentially offset from first position). Encoder 204 comprises an encoder wheel 206 on or extending through surface 210. As the endoscope 102 rotates within the channel 209, encoder wheel 206 may rotate and encoder 204 detects the rotation of endoscope 102 (for example, rotation about the longitudinal axis of endoscope 102). Encoder 205 comprises an encoder wheel 208 on or extending through surface 210. As endoscope 102 moves within channel 209, encoder wheel 208 may rotate and encoder 205 detects the advancement/withdrawal of endoscope 102 in the proximal/distal directions.

A controller 220 is connected to encoder 204 and encoder 205. Controller 220 is configured to track the rotational and proximal-distal movement based on input from encoder 204 and encoder 205, respectively. Controller 220 may record or otherwise determine a position of the endoscope from a baseline (e.g., Zero Point position) set by the user. Controller 220 is configured to determine the change in rotation and proximal-distal movement relative to the established Zero Point position and orientation.

An input device 222 is connected to controller 220. Input device 222 may be a button, keyboard, microphone, mouse, or any device that can be used to send instructions to controller 220. For example, the user may give a physical command (pressing a button) or a verbal command.

Input device 222 is further connected to a display 224. The change in rotation, and proximal-distal movement relative to an established Zero Point position may be output onto display 224. Display 224 may show two outputs, e.g., one output for rotation (e.g., degrees of rotation and direction, e.g., −360° to 360°) and a second output for proximal-distal movement (e.g., a unit of distance such as centimeters or inches).

Figure 2B:
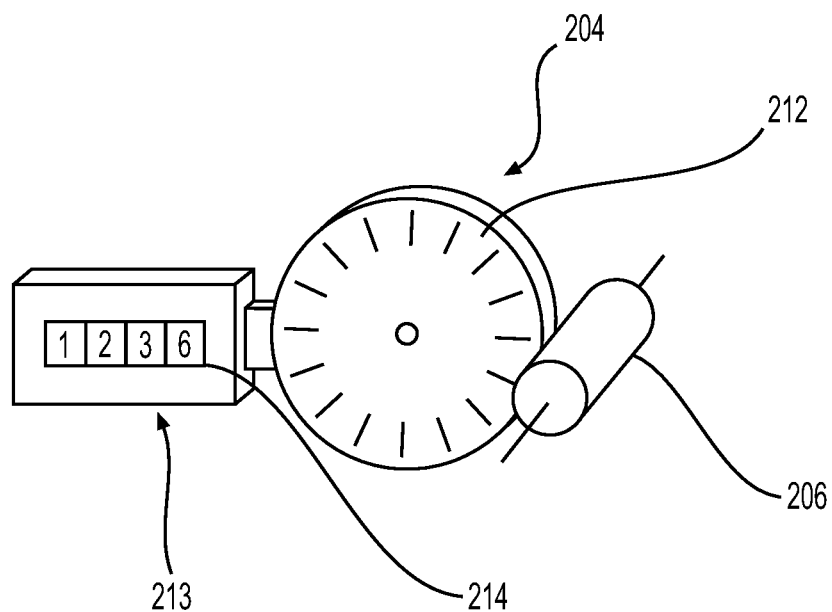

FIG. 2B depicts encoder 204 and encoder wheel 206. Encoder 204 may further comprise a rotating disk 212 and a sensor 213. Rotation of encoder wheel 206 causes the rotation of the rotating disk 212, which is detected by sensor 213. Sensor 213 converts the rotation of the rotating disk 212 to a numerical output. Sensor 213 may further comprise a display 214 to show a numerical output to the physician.

Figure 3A:
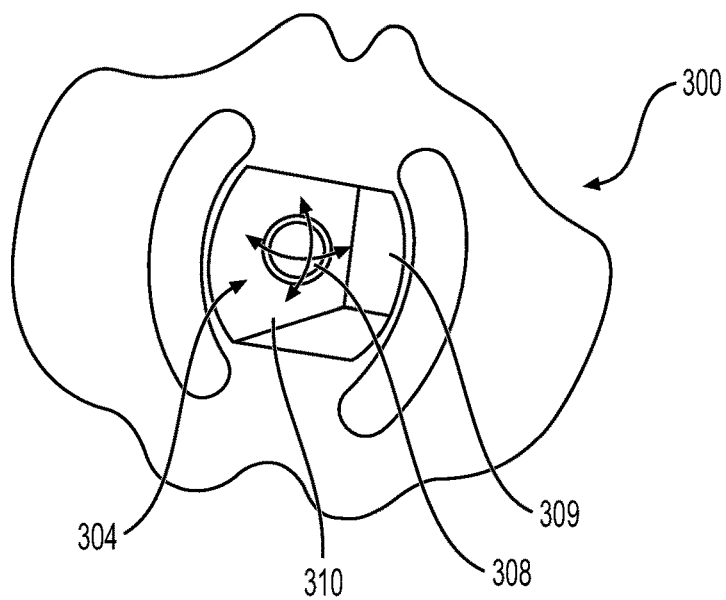
FIGS. 3A-3B illustrate another exemplary encoder system.

FIG. 3A depicts a bite block 300, which may be substantially similar to bite block 200. In the embodiment shown in FIGS. 3A-3B, bite block 300 includes an encoder 304. Channel 309 may be defined circumferentially by one or more surfaces. In one embodiment, channel 309 may have a generally circular cross-section, although other suitable cross-sections also are contemplated. Encoder 304 may extend through the surface 310 that defines channel 309 and includes a mechanical ball 308. Encoder 304 may be configured to rotate about a first axis 350 and a second axis 352 that is perpendicular to axis 350. First axis 350 may be substantially parallel with a central longitudinal axis of channel 309 that extends through channel 309 in the proximal-distal direction. Second axis 352 may extend vertically so that it extends substantially parallel to face of channel 209. Second axis 352 may be substantially perpendicular to first axis 350.

Endoscope 102 shown in FIG. 1, may be extended through channel 309 in the proximal-distal direction and also rotated within channel 309.

Figure 3B:
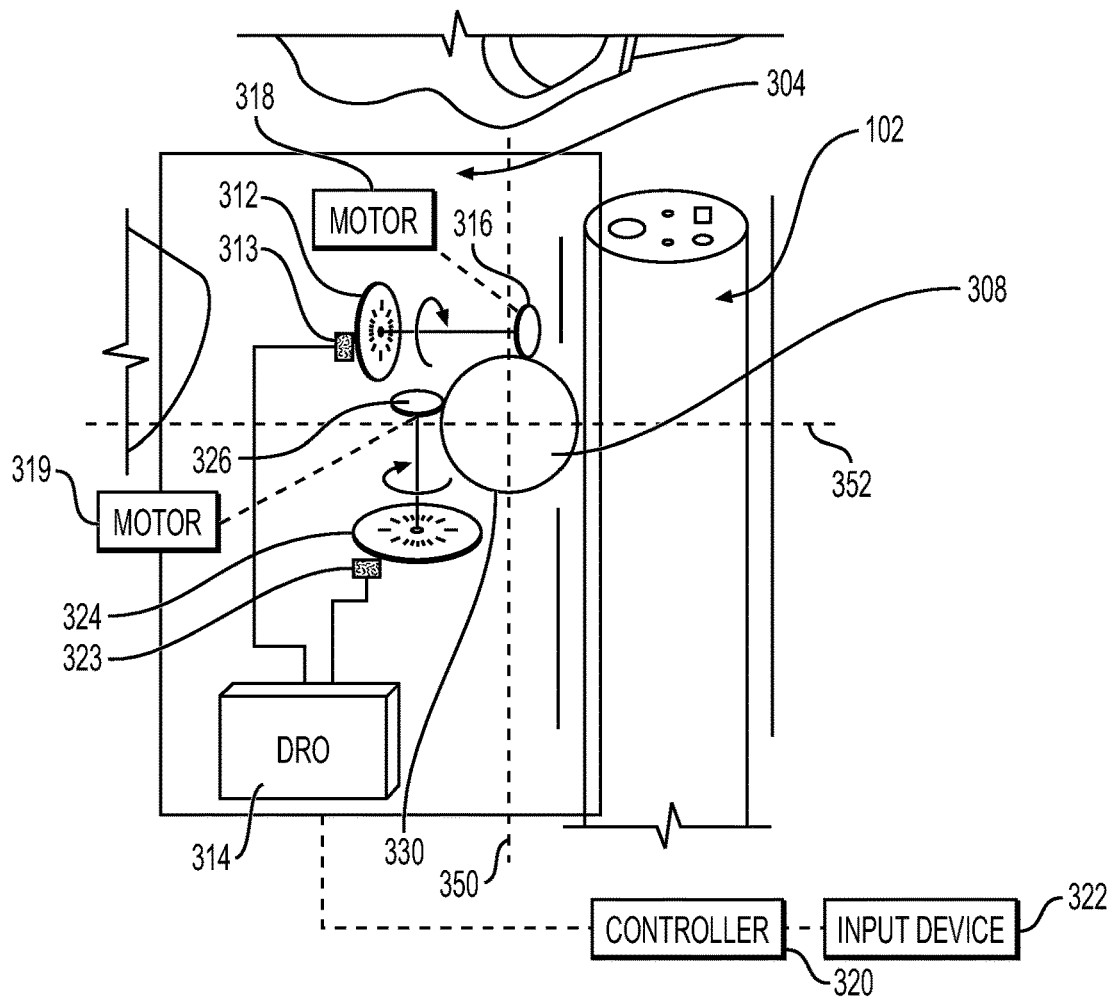

FIG. 3B depicts an encoder 304. Encoder 304 may include a first rotating disk 312 coupled to a first wheel 316 so that as mechanical ball 308 rotates about second axis 352 so does rotating disk 312. First rotating disk 312 and first wheel 316 may be positioned to rotate about an axis parallel to axis 352. First wheel 316 contacts an outside surface 330 of mechanical ball 308. Rotation of mechanical ball 308 about second axis 352 causes first wheel 316 and first rotating disk 312 to rotate. A first sensor 313 may be positioned next to first rotating disk 312 and detects proximal-distal movement of endoscope 102.

Encoder 304 may also include a second rotating disk 324 coupled to a second wheel 326 so that as mechanical ball 308 rotates about first axis 350 so does second rotating disk 324. Second rotating disk 324 and second wheel 326 may be positioned to rotate about an axis parallel to axis 350. Second wheel 326 contacts outside surface 330 of mechanical ball 308. Rotation of mechanical ball 308 about first axis 350 causes second wheel 326 and second rotating disk 324 to rotate. A second sensor 323 may be positioned next to second rotating disk 324 and detects rotation of endoscope 102.

Sensor 313 and sensor 323 may be coupled to a display 314 that shows the numeric output for rotational (e.g., degrees of rotation and direction, e.g., −360° to 360°) and proximal-distal movement (e.g., a unit of distance such as centimeters or inches) of endoscope 102.

In one embodiment, a motor 318 is coupled to first wheel 316 and a motor 319 is coupled to second wheel 326. Motor 318 is configured to drive rotation of first wheel 316 about an axis parallel to second axis 352, which drives rotation of mechanical ball 308 about second axis 352 and thus proximal-distal movement of endoscope 102. Motor 319 is configured to drive rotation of second wheel 326 about an axis parallel to first axis 350, which drives rotation of mechanical ball 308 about first axis 350 and thus rotation of endoscope 102.

A controller 320 is connected to encoder 304, motor 318, and motor 319. Controller 320 is configured to track the rotational and proximal-distal movement of endoscope 102 based on input from encoder 304. Controller 320 may record or otherwise determine a change in position of the endoscope 102 from a baseline (e.g., Zero Point position) set by the user. Controller 320 is configured to determine the change in rotation and proximal-distal movement relative to an established Zero Point position.

Controller 320 is further connected to an input device 322. Input device 322 may be used to instruct controller 320 to return endoscope 102 to the Zero Point position, for example, automatically or upon receiving instruction from a user. Then, motor 318 coupled to first wheel 316 and motor 319 coupled to second wheel 326 drive rotation of mechanical ball 308 in order to drive endoscope 102 to the Zero Point position. This is done by reducing and eventually substantially eliminating deviation of rotational movement and of proximal-distal movement since the point in time that the Zero Point position and orientation was set. Controller 320 tracks the rotation and proximal-distal movement of endoscope 102 through encoder 304 to ensure endoscope 102 reaches the Zero Point position.

Figure 4A:
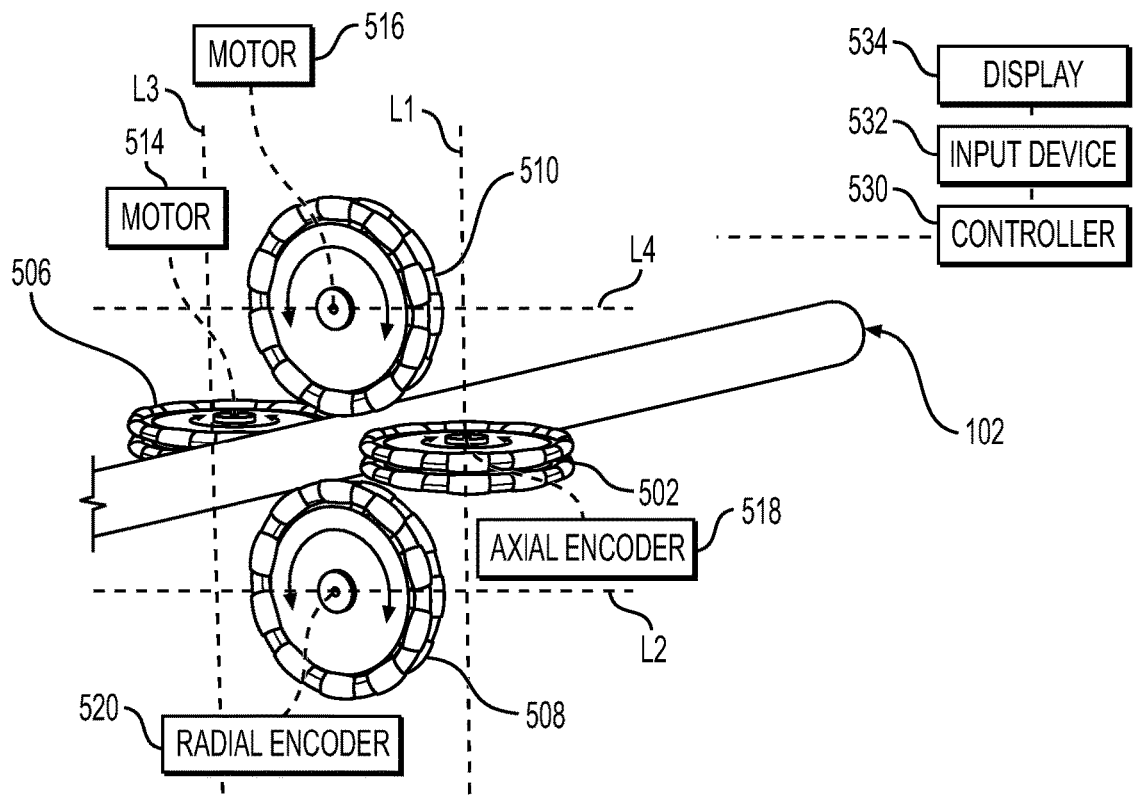
FIGS. 4A-4B illustrate other exemplary encoder systems.
Figure 4B:
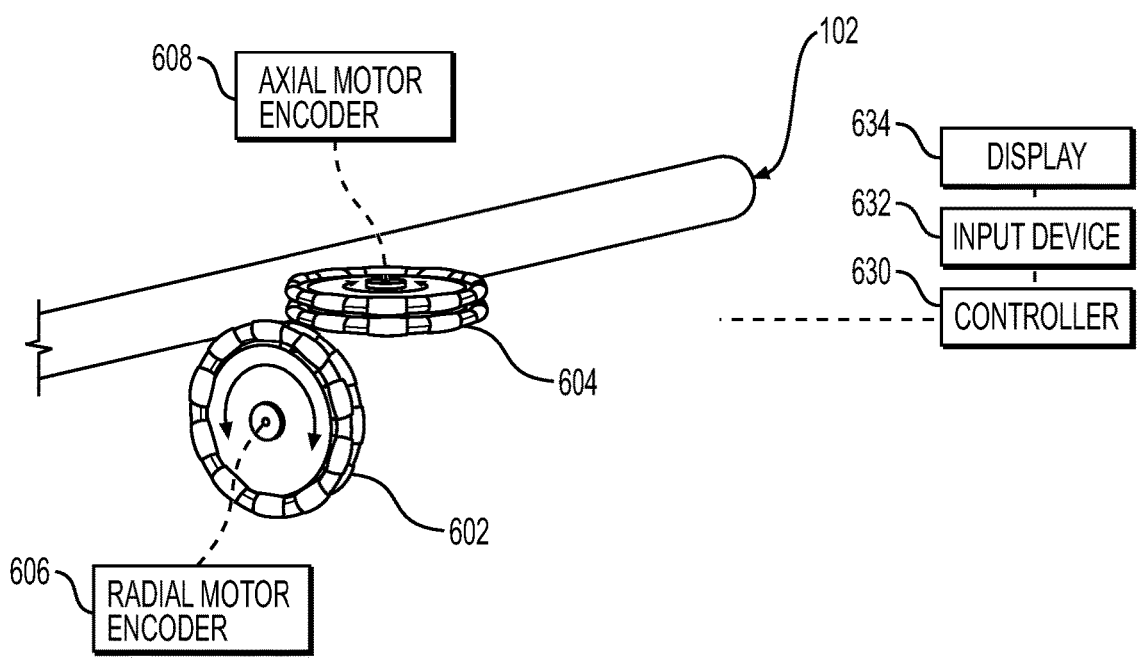

FIGS. 4A and 4B depict multi-directional wheels that may act as encoders and/or mechanical wheels that can drive the rotation and proximal-distal movement of endoscope 102. Multi-directional wheels may allow for rotation in both "forward-backward" and "side-to-side" directions. In FIG. 4A, an axial encoding multi-directional wheel 502 is positioned in contact with endoscope 102 and relative to endoscope 102 such that proximal-distal movement of endoscope 102 will cause axial encoding multi-directional wheel 502 to rotate about an axis L1. An axial encoder 518 is operably coupled with axial encoding multi-directional wheel 502 such that axial encoder 518 is able to detect when axial encoding multi-directional wheel 502 rotates. An axial driving multi-directional wheel 506 is operably coupled with a motor 514. Axial driving multi-directional wheel 506 may rotate about an axis L3. Axial driving multi-directional wheel 506 is positioned in contact with endoscope 102 and relative to endoscope 102 such that motor 514 is able to drive the proximal-distal movement of endoscope 102.

Similarly, a radial encoding multi-directional wheel 508 is positioned in contact with endoscope 102 and relative to endoscope 102 such that rotation of endoscope 102 about its own longitudinal axis will cause radial encoding multi-directional wheel 508 to rotate about an axis L2 that is substantially parallel to longitudinal axis of endoscope 102. A radial encoder 520 is operably coupled with radial encoding multi-directional wheel 508 such that radial encoder 520 is able to detect when radial encoding multi-directional wheel 508 rotates. A radial driving multi-directional wheel 510 is operably coupled with a motor 516. Radial driving multi-directional wheel 510 may rotate about an axis L4. Radial driving multi-directional wheel 510 is positioned in contact with endoscope 102 and relative to endoscope 102 such that motor 516 is able to drive the rotation of endoscope 102 about its own longitudinal axis.

It will be appreciated that axial encoding multi-directional wheel 502 and radial encoding multi-directional wheel 508 are arranged such that axis L1 is orthogonal to axis L2. Similarly, it will be appreciated that axial driving multi-directional wheel 506 and radial driving multi-directional wheel 510 are arranged such that axis L3 is orthogonal to axis L4. It will also be appreciated that axis L1 is substantially parallel to axis L3 and axis L2 is substantially parallel to axis L4.

Axial encoding multi-directional wheel 502 may be positioned on one side of the bite block and axial driving multi-directional wheel 506 may be positioned on the opposite side of the bite block, for example. Radial encoding multi-directional wheel 508 may be positioned on the bottom of the bite block and radial driving multi-directional wheel 510 may be positioned on the opposite side of the bite block, for example.

It will be appreciated that motion of either axial encoding multi-directional wheel 502 or radial encoding multi-directional wheel 508, or both, may be communicated to a controller 530. Controller 530 is configured to track the rotational and proximal-distal movement of endoscope 102 based on input from axial encoder 518 and radial encoder 520. Controller 530 is connected to an input device 532 and a display 534 to display the numeric output for rotational (e.g., degrees of rotation and direction, e.g., −360° to 360°) and proximal-distal movement (e.g., a unit of distance such as centimeters or inches) of endoscope 102.

In response to detecting movement of axial encoding multi-directional wheel 502, axial encoder 518 sends a communication informing the controller 530. Similarly, in response to detecting movement of radial encoding multi-directional wheel 508, radial encoder 520 sends a communication informing controller 530. Axial encoder 518 and radial encoder 520 may take any form. Axial encoder 518 and/or radial encoder 520 may be a mechanical encoder, for example. The rotational (e.g., degrees of rotation and direction, e.g., −360° to 360°) and proximal-distal movement (e.g., a unit of distance such as centimeters or inches) detected are output onto display 534. Input device 532 may be used to set a Zero Point position for endoscope 102. As endoscope 102 moves, axial encoder 518 and radial encoder 520 detect change in rotation (e.g., degrees of rotation and direction, e.g., −360° to 360°) and proximal-distal movement (e.g., a unit of distance such as centimeters or inches) relative to an established Zero Point position and may be output onto display 534.

Controller 530 is coupled to axial driving multi-directional wheel 506 and radial driving-multidirectional wheel 510. Input device 532 may be used to instruct controller 530 to return endoscope 102 to the Zero Point position, for example, automatically or upon receiving instruction from a user. Then, axial driving multi-directional wheel 506 and radial driving-multidirectional wheel 510 drive endoscope 102 to the Zero Point position by reducing and eventually substantially eliminating deviation of rotational movement and of proximal-distal movement since the point in time that the Zero Point position and orientation was set. Controller 530 tracks the rotation and proximal-distal movement of endoscope 102 through axial encoding multi-directional wheel 502 and radial encoding multi-directional wheel 508 to ensure endoscope 102 reaches the Zero Point position.

FIG. 4B depicts a similar system shown in FIG. 4A. FIG. 4B depicts two multi-directional wheels that act as both encoders and drivers. A radial multi-directional wheel 602 is operably coupled to a radial motor encoder 606. Radial multi-directional wheel 602 is configured to detect and drive rotation of endoscope 102. An axial multi-directional wheel 604 is operably coupled to an axial motor encoder 608. Axial multi-directional wheel 604 is configured to detect and drive proximal-distal movement of endoscope 102.

Radial multi-directional wheel 602 may be positioned on either top or bottom of a bite block, for example. Axial multi-directional wheel 604 may be positioned on either side of the bite block, for example. Radial multi-directional wheel 602 and axial multi-directional wheel 604 may be positioned opposite of one another, for example. Radial multi-directional wheel 602 may be positioned on top of the bite block and axial multi-directional wheel 604 may be positioned at the bottom of the bite block, for example. Radial multi-directional wheel 602 may be positioned on one side of the bite block and axial multi-directional wheel 604 may be positioned on the opposite side of the bite block, for example.

The system in FIG. 4B includes a controller 630, an input device 632, and a display 634 that operate similarly to the controller, input device, and display in FIG. 4A.

Figure 5:
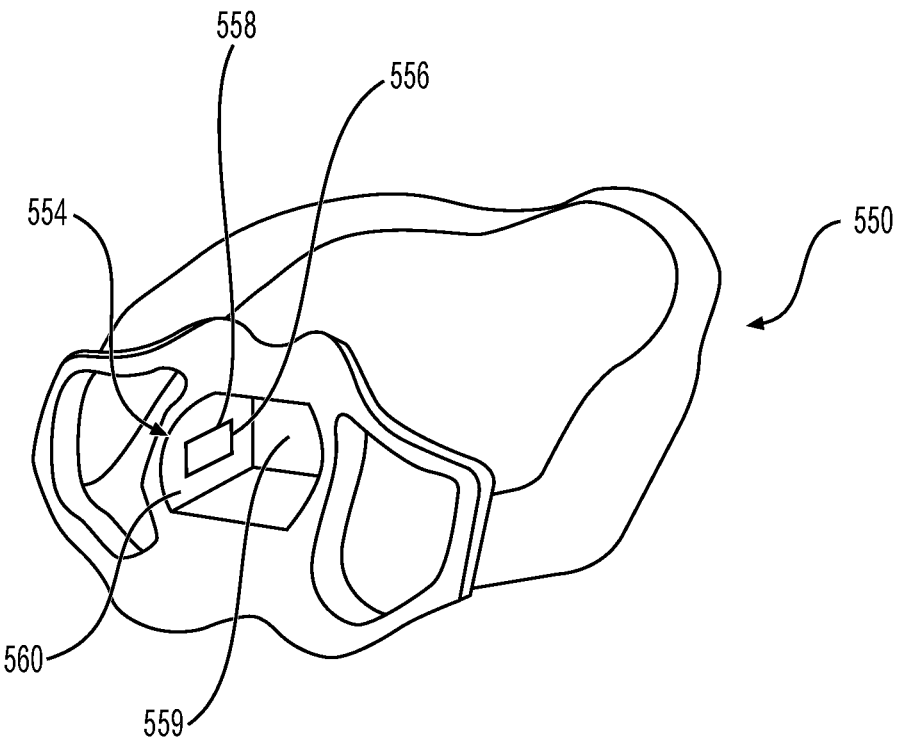
FIG. 5 illustrates another exemplary encoder system.

FIG. 5 depicts a bite block 550. Bite block 550 may include one encoder configured to determine and/or track the relative movement and position of an endoscope or other elongate medical device extending through a channel 559 of bite block 550. In the embodiment shown in FIG. 5, bite block 550 includes an encoder 554. Channel 559 may be defined circumferentially by one or more surfaces. In one embodiment, channel 559 may have a generally circular cross-section, although other suitable cross-sections also are contemplated. Encoder 554 may be positioned on or extend through the surface 560 that defines channel 559.

Encoder 554 may include a magnet 558 and a Hall effect sensor 556. Hall effect sensor 556 may be positioned on surface 560 facing the inside of channel 559. Magnet 558 may be positioned behind Hall effect sensor 556 so that Hall effect sensor 556 sits in a permanent and static magnetic field. The Hall effect sensor 556 is configured to detect the rotational and proximal-distal movement of endoscope 102 made of a ferromagnetic material by detecting changes in the magnetic field. The movement of endoscope 102 made of ferromagnetic material is then converted to an output voltage being directly proportional to the magnetic field passing through the Hall effect sensor 556.

Figure 6:
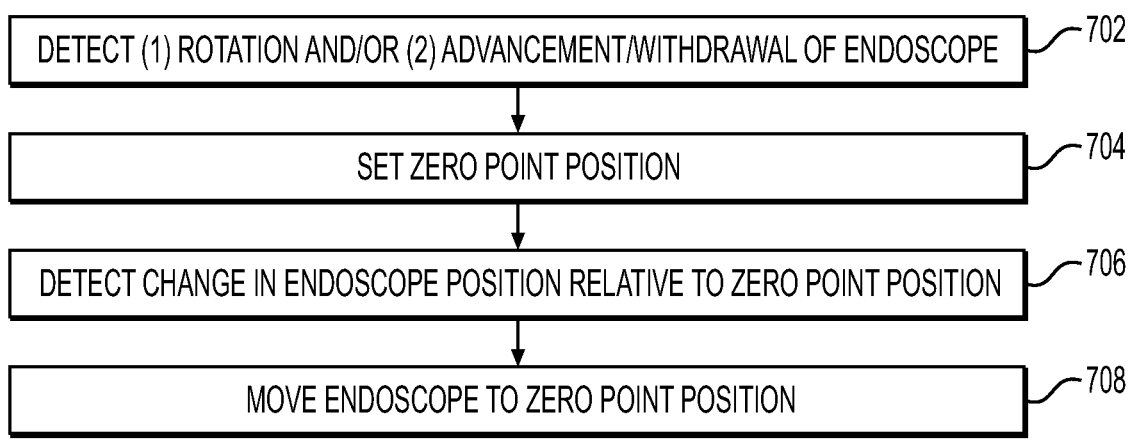
FIG. 6 is a flowchart of an exemplary method for detecting and setting a baseline or Zero Point position of an endoscope, according to one or more embodiments.

FIG. 6 is a flowchart of an exemplary method for detecting and setting a Zero Point position of an endoscope, according to one or more embodiments. Any of the encoder systems described above may be used in this method. A bite block is placed in a patient's mouth and may be secured using a strap. An endoscope is then extended through a channel in the bite block in the proximal-distal direction. In Step 702, an encoder may detect rotation and/or advancement/withdrawal of the endoscope. For example, one or more encoders may detect rotation of the endoscope in the clockwise or counterclockwise direction. One or more encoders may detect proximal-distal movement of the endoscope. One or more encoders may communicate rotational and/or proximal-distal movement of endoscope as a numeric output to a controller. The numeric output received by the controller from the one or more encoders may also be shown on a display that can be viewed by a user.

In Step 704, once the user has found a desired position of the endoscope, the user can instruct the controller to set the desired position of the endoscope as a Zero Point position of the endoscope. In a manner similar to 'zeroing' a scale, the rotation and proximal-distal values may be zeroed. Desired position may be when a distal end of endoscope is at or adjacent to papilla. Instructions may be sent to the controller using an input device such as a button. In Step 706, the one or more encoders may detect proximal-distal movement and/or rotation of the endoscope and communicate the numerical outputs to the controller so that the controller can track the change in endoscope position relative to the Zero Point position. In Step 708, a user may move the endoscope to the Zero Point position manually and visually confirm that the endoscope has reached the Zero Point position by viewing the numerical output shown on the display. A user may also instruct the controller to automatically return the endoscope to the Zero Point position, for example, by using one or more motors to return the endoscope to the Zero Point position. In an auto-zero mode, the controller may continuously use the one or more motors to drive endoscope 102 to the set Zero Point position continuously.

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

What is claimed is:

1. A system for tracking a medical device, the system comprising:
   a support having a channel extending therethrough, the channel being defined circumferentially by a surface;
   at least one encoder including a first wheel configured to track movement of a medical device through the channel;
   a second wheel configured to drive the medical device; and
   one or more processors configured to:
      receive input from the at least one encoder;
      receive an instruction from a user to store a zero position of the medical device relative to the channel;
      determine relative movement of the medical device from the zero position; and
      communicate the relative movement of the medical device from the zero position to cause the second wheel to drive the medical device to the zero position, wherein the first wheel tracks displacement of the medical device to ensure the medical device returns to the zero position in response to any deviation.

2. The system of claim 1, wherein the at least one encoder includes a movable portion extending through or positioned at the surface defining the channel.

3. The system of claim 1, wherein determining the relative movement includes determining a proximal and/or a distal movement of the medical device relative to a proximal and/or distal position of the medical device at the zero position.

4. The system of claim 1, wherein determining the relative movement includes determining rotation of the medical device relative to a rotational orientation of the medical device at the zero position.

5. The system of claim 1, wherein the first wheel is a first encoder wheel configured to measure proximal and/or distal movement of the medical device, and wherein the at least one encoder further includes a second encoder wheel configured to measure rotation of the medical device about a central longitudinal axis of the medical device.

6. The system of claim 1, wherein the at least one encoder includes a ball contacting at least the first wheel, and the at least one encoder is configured to measure proximal and/or distal movement and rotation of the medical device based on movement of the ball.

7. The system of claim 1, wherein the support is a bite block configured to be secured to a face and/or a mouth of a patient.

8. The system of claim 1, further including a motor coupled to the one or more processors and to at least the second wheel, wherein the one or more processors are further configured to cause the second wheel to drive the medical device to the zero position by activating the motor.

9. The system of claim 8, wherein causing the second wheel to drive the medical device to the zero position includes moving, by the second wheel, the medical device proximally and/or distally.

10. The system of claim 8, wherein causing the second wheel to drive the medical device to the zero position includes rotating, by the second wheel, the medical device.

11. The system of claim 8, wherein the motor is configured to be coupled to the medical device via the second wheel or a ball contacting the second wheel.

12. The system of claim 11, wherein the second wheel or the ball is separate from the first wheel that forms part of the at least one encoder.

13. The system of claim 11, wherein the second wheel or the ball forms part of the at least one encoder.

14. The system of claim 1, wherein communicating the relative movement further includes sending a relative proximal and/or distal displacement and sending a relative rotational displacement from the zero position to a display device.

15. A system for tracking a medical device, the system comprising:
a support having a channel extending therethrough, the channel being defined circumferentially by a surface;
at least one first wheel coupled to at least one encoder and configured to track movement of the medical device through the channel;
at least one second wheel coupled to a motor and configured to drive the medical device through the channel; and
one or more processors configured to:
receive input from the at least one encoder;
receive an instruction from a user to store a zero position of the medical device relative to the channel;
determine relative movement of the medical device from the zero position; and
communicate the relative movement of the medical device from the zero position to cause the at least one second wheel to drive the medical device to the zero position, wherein the at least one first wheel tracks displacement of the medical device to ensure the medical device returns to the zero position in response to any deviation.

16. A method for tracking a medical device, the method comprising:
receiving an instruction from a user to store a current, zero position of a medical device;
measuring movement of the medical device relative to the zero position using at least one encoder wheel; and
moving the medical device back to the zero position by causing at least one driving wheel to drive the medical device to the zero position, wherein the at least one encoder wheel tracks displacement of the medical device to ensure the medical device returns to the zero position in response to any deviation.

17. The method of claim 16, wherein measuring the movement of the medical device relative to the zero position includes measuring proximal and/or distal movement and rotation of the medical device relative to the zero position using the at least one encoder wheel.

* * * * *